(12) United States Patent
Imaizumi et al.

(10) Patent No.: US 11,197,807 B2
(45) Date of Patent: Dec. 14, 2021

(54) GEL-TYPE OIL-IN-WATER EMULSION COMPOSITION

(71) Applicant: FUJIFILM CORPORATION, Tokyo (JP)

(72) Inventors: Yuki Imaizumi, Tokyo (JP); Toshiaki Kubo, Tokyo (JP)

(73) Assignee: FUJIFILM CORPORATION, Tokyo (JP)

(*) Notice: Subject to any disclaimer, the term of this patent is extended or adjusted under 35 U.S.C. 154(b) by 182 days.

(21) Appl. No.: 16/655,270

(22) Filed: Oct. 17, 2019

(65) Prior Publication Data

US 2020/0046615 A1 Feb. 13, 2020

Related U.S. Application Data

(63) Continuation of application No. PCT/JP2018/016377, filed on Apr. 20, 2018.

(30) Foreign Application Priority Data

Apr. 21, 2017 (JP) ............................ JP2017-084876

(51) Int. Cl.
| | |
|---|---|
| A61K 8/06 | (2006.01) |
| A61K 8/04 | (2006.01) |
| A61K 8/25 | (2006.01) |
| A61K 8/36 | (2006.01) |
| A61K 8/362 | (2006.01) |
| A61K 8/60 | (2006.01) |
| A61K 8/92 | (2006.01) |
| A61Q 19/00 | (2006.01) |

(52) U.S. Cl.
CPC ............. *A61K 8/062* (2013.01); *A61K 8/042* (2013.01); *A61K 8/25* (2013.01); *A61K 8/361* (2013.01); *A61K 8/362* (2013.01); *A61K 8/60* (2013.01); *A61K 8/92* (2013.01); *A61Q 19/007* (2013.01)

(58) Field of Classification Search
CPC ...... A61Q 19/00; A61Q 19/007; A61Q 17/04; A61Q 1/02; A61Q 1/06; A61Q 19/02; A61Q 19/08; A61Q 7/00; A61Q 15/00; A61Q 19/04; A61Q 5/00; A61K 8/361; A61K 8/39; A61K 8/062; A61K 2800/21; A61K 8/06; A61K 8/31; A61K 8/37; A61K 8/375; A61K 8/891; A61K 2800/262; A61K 8/553; A61K 8/68; A61K 2800/596; A61K 8/042; A61K 8/25; A61K 8/345; A61K 8/362; A61K 8/44; A61K 8/60; A61K 8/92; A61K 47/18; A61K 8/34; A61K 8/9789; A61K 9/0014; A61K 9/1075; A61K 2800/413; A61K 2800/56; A61K 8/0241; A61K 8/342; A61K 8/35; A61K 8/42; A61K 8/498; A61K 8/64; A61K 8/73; A61K 8/86; A61K 8/9711; A61K 8/9717; A61K 8/9722; A61K 8/9728; A61K 8/9733; A61K 8/9767; A61K 8/9771; A61K 8/9783; A61K 8/9794; A61K 9/107; Y10S 514/937; Y10S 514/938
See application file for complete search history.

(56) References Cited

U.S. PATENT DOCUMENTS

| | | |
|---|---|---|
| 2001/0053376 A1 | 12/2001 | Iwai et al. |
| 2004/0081633 A1 | 4/2004 | Mercier et al. |

FOREIGN PATENT DOCUMENTS

| | | | |
|---|---|---|---|
| EP | 2818157 A1 | 12/2014 | |
| EP | 2982364 A1 | 2/2016 | |
| EP | 3173064 A1 | 5/2017 | |
| JP | H08-127526 A | 5/1996 | |
| JP | 2001-342113 A | 12/2001 | |
| JP | 2002-087931 A2 | 3/2002 | |
| JP | 2008-094723 A | 4/2008 | |
| JP | 2010-143858 A | 7/2010 | |
| JP | 2010143858 A * | 7/2010 | ............... A61K 8/44 |
| JP | 2013-199466 A | 10/2013 | |
| JP | 2014-201558 A | 10/2014 | |
| JP | 2015-030705 A | 2/2015 | |
| JP | 2017-105766 A | 6/2017 | |
| JP | 2017-119640 A | 7/2017 | |
| WO | 2012/172425 A1 | 12/2012 | |
| WO | 2014/98268 A1 | 6/2014 | |

OTHER PUBLICATIONS

International Search Report issued in International Application No. PCT/JP2018/016377 dated Jul. 24, 2018.
Written Opinion of the ISA issued in International Application No. PCT/JP2018/016377 dated Jul. 24, 2018.
Furusawa, Kunio (supervisor), "New Technology and Applications of Dispersion & Emulsion Systems", Techno System Co., Ltd., pp. 808-811 (2006).
Extended European Search Report dated Mar. 11, 2020, issued in corresponding EP Patent Application No. 18787676.8.

(Continued)

*Primary Examiner* — Audrea B Coniglio
(74) *Attorney, Agent, or Firm* — Solaris Intellectual Property Group, PLLC

(57) ABSTRACT

Provided is a gel-type oil-in-water emulsion composition containing components A to F, in which A: at least one liquid oil which is selected from the group consisting of a hydrocarbon oil, an aliphatic ester and a silicone oil and a content of which is equal to or greater than 15% by mass with respect to a total amount of the gel-type oil-in-water emulsion composition; B: at least one nonionic surfactant which is selected from the group consisting of a saturated fatty acid glyceryl and a saturated fatty acid polyglyceryl and which has a Hydrophilic-Lipophilic Balance of equal to or smaller than 7; C: a sucrose saturated fatty acid ester; D: an ionic surfactant which has a saturated fatty acid residue as a hydrophobic group and a glutamic acid residue as a hydrophilic group; E: at least one surfactant having an unsaturated fatty acid residue; and F: water.

6 Claims, No Drawings

(56) References Cited

OTHER PUBLICATIONS

English language translation of the following: Office action dated Jul. 7, 2020 from the JPO in a Japanese patent application No. 2019-513714 corresponding to the instant patent application.

* cited by examiner

GEL-TYPE OIL-IN-WATER EMULSION COMPOSITION

CROSS-REFERENCE TO RELATED APPLICATIONS

This application is a continuation application of International Application No. PCT/JP2018/016377, filed Apr. 20, 2018, the disclosure of which is incorporated herein by reference in its entirety. Further, this application claims priority from Japanese Patent Application No. 2017-084876, filed Apr. 21, 2017, the disclosure of which is incorporated herein by reference in its entirety.

BACKGROUND OF THE INVENTION

1. Field of the Invention

The present invention relates to a gel-type oil-in-water emulsion composition.

2. Description of the Related Art

Generally, for the purpose of moisturizing skin, oleaginous components are mixed with external preparations for skin such as cosmetics. The external preparations for skin such as emulsion and cream mixed with large amounts of oleaginous components look white and lack transparency. Accordingly, such preparations give an impression of being very oily and tend not to be easily accepted by people who want moistness, transparency, and the like.

Meanwhile, external preparations for skin such as toner and aqueous gel having excellent transparency are usually mixed with oleaginous components by exploiting a solubilizing performance of a surfactant. Therefore, it is difficult for such preparations to be mixed with large amounts of oleaginous components. As a result, generally, in external preparations for skin having excellent transparency, a moisturizing effect and a skin care effect brought about by oleaginous components tend to be weaker than those in emulsion, cream, and the like containing large amounts of oleaginous components.

Accordingly, there is a demand for an emulsion composition useful for external preparations for skin that can contain oleaginous components in an amount sufficient for fully obtaining moisturizing properties brought about by the oleaginous components and has excellent transparency.

As one of the manufacturing methods of emulsion cosmetics containing large amounts of oleaginous components and maintaining transparency, a method of using a high-pressure emulsification apparatus has been reported (see "New Technology and Applications of Dispersion & Emulsion Systems", supervised by Kunio Furusawa, Techno System Co., Ltd., pp. 808 (2006)). Non-Patent Literature 1 describes a method for preparing an emulsion composition which contains large amounts of oleaginous components and maintains transparency by making the oleaginous components into nanostructured emulsion particles by using a high-pressure emulsification apparatus. In a case where the high-pressure emulsification apparatus is used, a nano-emulsion of nanostructured emulsion particles containing certain amounts of oleaginous components is formed. As the number of emulsion particles per unit volume increases, a distance between the emulsion particles is reduced, and accordingly, the nano-emulsion is packed with the emulsion particles. Non-Patent Literature 1 describes that consequently, the emulsion particles repel each other to induce orientation of the particles, which causes viscosity increase due to the increase in repulsive force between the particles, so that the emulsion composition becomes a gel state.

As an emulsion composition that looks transparent, an oil-in-water type emulsion composition has been suggested which is formed of oil drops each having a lamellar liquid crystal film, that is, a thin-film type liquid crystal film and dispersed in an aqueous phase (see JP1996-127526A (JP-H08-127526A)).

Furthermore, a gel-type essence has been suggested which contains a specific surfactant, is transparent, has excellent texture, and can contain large amounts of oleaginous components (see JP2002-087931A and JP2001-342113A).

In addition, as a ceramide dispersion composition having excellent temporal stability, a ceramide dispersion has been suggested which contains particles, obtained by dispersing a sucrose fatty acid ester, a nonionic surfactant, and natural ceramide as an oil phase in a water phase, and has a pH equal to or lower than 6.5 (see JP2015-030705A).

Moreover, a composition has been suggested which contains water and liposomes containing a water-soluble silk protein with improved temporal stability (see JP2008-094723A).

SUMMARY OF THE INVENTION

Although the emulsion compositions described in JP1996-127526A (JP-H08-127526A) and JP2002-087931A are transparent and have excellent emulsion stability, it is difficult to obtain a gel-type composition from the emulsion compositions. JP2001-342113 describes that a transparent emulsion composition is obtained by a technique disclosed in the document, and the emulsion composition can be made into a gel-type essence by adding a thickener. However, in a case where the emulsion composition is made into a gel-type formulation by adding a thickener, in many cases, the formulation becomes sticky due to the thickener.

Although the dispersion described in JP2015-030705A is transparent, because the dispersion contains a salt, it is difficult to obtain a gel-type dispersion from the dispersion.

In addition, the dispersion composition described in JP2008-094723A cannot be a gel-type formulation because the content of oleaginous components in the dispersion composition with respect to the total amount of the composition is small.

The gel-type emulsion composition formed of the nano-emulsion described in "New Technology and Applications of Dispersion & Emulsion Systems", supervised by Kunio Furusawa, TECHNO SYSTEM CO., LTD., pp. 808 (2006) (hereinafter, referred to as Literature A) becomes a gel state by the repulsive force between the emulsion particles. Therefore, due to the contact with a salt or the aggregation of the emulsion particles with the passage of time, sometimes the gel-type formulation is disrupted.

From the viewpoint of being used as external preparations for skin such as cosmetics applied to skin, the gel-type emulsion composition described in Literature A is expected to spread well because the gel state is disrupted simply by being applied to skin. Literature A describes that due to the prompt state change from the gel state to a liquid on skin, a gel-type emulsion composition having excellent texture is obtained.

However, as described above, sometimes the formulation of the gel-type emulsion composition described in Literature A is disrupted due to the contact with a salt, the change in a particle diameter of the emulsion particles, and the like.

Accordingly, for example, it is apprehended that in a case where the composition is applied to external preparations for skin and the like, sufficient storage stability may not be obtained.

An object to be achieved by an embodiment of the present invention is to provide a gel-type oil-in-water emulsion composition which has excellent transparency, excellent temporal stability, and excellent texture in a case where the composition is applied to skin.

Means for achieving the object include the following embodiments.

<1> A gel-type oil-in-water emulsion composition comprising the following components A to F: A: at least one liquid oil which is selected from the group consisting of a hydrocarbon oil, an aliphatic ester and a silicone oil and a content of which is equal to or greater than 15% by mass with respect to a total amount of the gel-type oil-in-water emulsion composition; B: at least one nonionic surfactant which is selected from the group consisting of a saturated fatty acid glyceryl and a saturated fatty acid polyglyceryl and which has a Hydrophilic-Lipophilic Balance of equal to or smaller than 7; C: a sucrose saturated fatty acid ester; D: an ionic surfactant which has a saturated fatty acid residue as a hydrophobic group and a glutamic acid residue as a hydrophilic group; E: at least one surfactant having an unsaturated fatty acid residue; and F: water.

<2> The gel-type oil-in-water emulsion composition described in <1>, wherein the unsaturated fatty acid residue of the component E is selected from the group consisting of an oleic acid residue, a linoleic acid residue, and a linolenic acid residue.

<3> The gel-type oil-in-water emulsion composition described in <1> or <2> comprising two or more kinds of the component E.

<4> The gel-type oil-in-water emulsion composition described in any one of <1> to <3>, comprising one or more kinds of a nonionic surfactant as the component E.

<5> The gel-type oil-in-water emulsion composition described in any one of <1> to <4>, comprising one or more kinds of an amphoteric surfactant as the component E.

<6> The gel-type oil-in-water emulsion composition described in any one of <1> to <5>, comprising a silicone oil as the component A, wherein a content of the silicone oil is 60% by mass to 95% by mass with respect to a total amount of the component A.

<7> The gel-type oil-in-water emulsion composition described in any one of <1> to <6>, comprising, as the components: one kind selected from a hydrocarbon oil; and two kinds selected from a silicone oil.

<8> The gel-type oil-in-water emulsion composition described in any one of <1> to <7>, wherein a content of the component E with respect to a content of the component B in the gel-type oil-in-water emulsion composition is from 0.1 to 3.0 based on mass.

According to an embodiment of the present invention, there is provided a gel-type oil-in-water emulsion composition which has excellent transparency, excellent temporal stability, and excellent texture in a case where the composition is applied to skin.

DESCRIPTION OF THE PREFERRED EMBODIMENTS

Hereinafter, the gel-type oil-in-water emulsion composition of the present disclosure will be specifically described by illustrating specific embodiments for example. However, the present invention is not limited to the following embodiments in the present disclosure, and can be embodied by being appropriately modified within the intended scope of the present invention.

In the present specification, a range of numerical values described using "to" is a range including the numerical values listed before and after "to" as a minimum value and a maximum value respectively.

In the present specification, in a case where there is a plurality of substances corresponding to each component in a composition, unless otherwise specified, the amount of each component in the composition means the total amount of the plurality of substances in the composition.

In the present specification, "room temperature" means 25° C.

Regarding the ranges of numerical values gradationally described in the present disclosure, an upper limit and a lower limit described in a certain range of numerical values may be substituted with an upper limit and a lower limit of another range of numerical values gradationally described. Furthermore, regarding the ranges of numerical values described in the present disclosure, an upper limit and a lower limit described in a certain range of numerical values may be substituted with the values described in Examples.

In the present specification, a combination of preferred aspects is a more preferred aspect.

<Gel-Type Oil-in-Water Emulsion Composition>

The gel-type oil-in-water emulsion composition of the present disclosure contains Component A to Component F.

A: at least one kind of liquid oil of which a content with respect to a total amount of the gel-type oil-in-water emulsion composition is equal to or greater than 15% by mass and which is selected from a hydrocarbon oil, an aliphatic ester, and a silicone oil.

B: at least one kind of nonionic surfactant which is selected from a saturated fatty acid glyceryl and a saturated fatty acid polyglyceryl and has an HLB equal to or smaller than 7.

C: a sucrose saturated fatty acid ester.

D: an ionic surfactant which has a saturated fatty acid residue as a hydrophobic group and a glutamic acid residue as a hydrophilic group.

E: at least one kind of surfactant having an unsaturated fatty acid residue.

F: water.

In the present specification, "gel-type oil-in-water emulsion composition" refers to an oil-in-water type emulsion composition which maintains its shape without exhibiting fluidity at room temperature in a state where a stress is not applied to the emulsion composition.

The hardness of the gel-type oil-in-water emulsion composition, which is measured using a rheometer generally used in the technical field relating to the present disclosure at room temperature, is preferably equal to or higher than 10 g.

Hereinafter, "gel-type oil-in-water emulsion composition of the present disclosure" will be referred to as "emulsion composition of the present disclosure" or simply referred to as "emulsion composition" in some cases.

By containing the components described above, the emulsion composition of the present disclosure has excellent transparency, excellent temporal stability, and excellent texture.

In the present specification, "transparent" and "transparency" mean that the composition looks transparent.

Turbidity can be used as a parameter for transparency, and can be determined by measuring an absorbance at a wavelength of 625 nm in a 1 cm cell. In the present disclosure, the transparency of the emulsion composition, which is represented by a turbidity determined by measuring an absorbance at a wavelength of 625 nm in a 1 cm cell by using, for example, an ultraviolet-visible absorptiometer manufactured by Shimadzu Corporation, is preferably less than 0.50, more preferably less than 0.25, and even more preferably less than 0.10. Furthermore, it is preferable that the emulsion composition of the present disclosure has excellent turbidity stability. That is, a difference between the turbidity of the emulsion composition measured immediately after the emulsion composition is prepared (initial turbidity) and the turbidity measured after the passage of a desired period of time is preferably less than 0.50.

In the present specification, "having excellent temporal stability" means that the gel state is maintained for a long period of time. Specifically, it is preferable that the hardness of the emulsion composition of the present disclosure is kept to be equal to or higher than 10 g for a desired period of time after the preparation of the emulsion composition.

In the present specification, "having excellent texture" means that in a case where the emulsion composition of the present disclosure is applied to skin, the emulsion composition does not feel oily to the touch, is excellently absorbed into skin, and gives moist texture to skin.

Hereinafter, the emulsion composition of the present disclosure including the components contained in the emulsion composition will be specifically described.

The emulsion composition of the present disclosure has a gel-type formulation.

Generally, in a case where a hardness, which is measured using a rheometer, of an emulsion composition is equal to or higher than 10 g, the fluidity of the emulsion composition is reduced, and the emulsion composition becomes a gel state.

The hardness of the emulsion composition of the present disclosure (hereinafter, referred to as gel hardness in some cases) is preferably equal to or higher than 10 g, more preferably equal to or higher than 25 g, and even more preferably equal to or higher than 50 g.

As a method for measuring the hardness of the emulsion composition, a known method can be adopted without particular limitation.

In the present specification, it is preferable to use a change in a maximum load, which is measured using a rheometer (FUDOH: RHEOTECH) and a 20 mmϕ disk-like probe at room temperature under the condition of a load of 200 g, a speed of 1 mm/sec, and an indentation depth of 20 mm, as the hardness of the emulsion composition (gel hardness). The arithmetic mean of values of hardness determined by performing the above operation three times is adopted as the hardness of the emulsion composition in the present specification.

[Component A: At Least One Kind of Liquid Oil of which Content with Respect to Total Amount of Oil-in-Water Emulsion Composition is Equal to or Greater than 15% by Mass and which is Selected from Hydrocarbon Oil, Aliphatic Ester, and Silicone Oil]

The emulsion composition of present disclosure contains A: at least one kind of liquid oil of which a content with respect to a total amount of the oil-in-water emulsion composition is equal to or greater than 15% by mass and which is selected from a hydrocarbon oil, an aliphatic ester, and a silicone oil.

In the present specification, "liquid oil" means an oleaginous component which remains in liquid state in an atmosphere with 25° C. and has a solubility equal to or lower than 0.1% by mass in water at 25° C.

The liquid oil contained in Component A is selected from a hydrocarbon oil, an aliphatic ester, and a silicone oil.

The hydrocarbon oil as the liquid oil in Component A may be an oil derived from animals or plants or a synthetic oil.

Examples of the hydrocarbon oil include squalane, liquid paraffin, hydrogenated polyisobutene, cyclohexane, and the like. Among these, hydrogenated polyisobutene, squalane, and the like are preferable because these have excellent moistness.

Examples of the aliphatic ester include an ester containing a fatty acid residue having 8 to 22 carbon atoms.

More specifically, examples of the aliphatic ester include isopropyl myristate, isopropyl palmitate, octyldodecyl myristate, myristyl myristate, butyl myristate, butyl stearate, isostearyl isostearate, diisopropyl sebacate, glyceryl tricaprylate/tricaprate, triethylhexanoin, triolein, and the like. Furthermore, olive oil, jojoba oil, and the like which are liquid oils derived from plants containing aliphatic esters are also included in the aliphatic ester in the present disclosure.

The silicone oil is not particularly limited as long as the silicone oil has a siloxane structure and remains in liquid state at 25° C.

Examples of the silicone oil include oleaginous components remaining in liquid state at 25° C., such as dimethicone, trisiloxane, cyclomethicone, cyclopentasiloxane, methyl trimethicone, caprylyl methicone, phenyl trimethicone, diphenyl dimethicone, and diphenylsiloxy phenyl trimethicone.

Among these, at least one kind of silicone oil selected from dimethicone, methyl trimethicone, caprylyl methicone, and cyclopentasiloxane is preferable, because the hardness of the emulsion composition tends to become suitable by such a silicone oil, and in a case where the emulsion composition is used as an external preparation for skin, such a silicone oil reduces stickiness and results in excellent texture.

As the silicone oil, a commercial product can be used.

Examples of commercial products of the silicone oil include KF-96L-1.5cs, KF-96L-2cs, KF-96A-5cs, and KF-96A-6cs (trade names) as dimethicone from Shin-Etsu Chemical Co., Ltd., and the like.

The emulsion composition may contain, as Component A, only one kind of liquid oil or two or more kinds of liquid oils. In a case where two or more kinds of liquid oils will be incorporated into the emulsion composition, liquid oils of the same type, that is, two or more kinds of liquid oils selected from hydrocarbon oils, two or more kinds of liquid oils selected from aliphatic esters, or two or more kinds of liquid oils selected from silicone oils may be used. Furthermore, two or more kinds of liquid oils selected from different types of liquid oils may be used. For example, at least one kind of liquid oil selected from hydrocarbon oils and at least one kind of liquid oil selected from aliphatic esters may be used in combination; at least one kind of liquid oil selected from hydrocarbon oils and at least one kind of liquid oil selected from silicone oils may be used in combination; or at least one kind of liquid oil selected from aliphatic esters and at least one kind of liquid oil selected from silicone oils may be used in combination. Alternatively, at least one kind of liquid oil selected from hydrocarbon oils, at least one kind of liquid oil selected from aliphatic esters, and at least one kind of liquid oil selected from silicone oils may be used in combination.

Particularly, from the viewpoint of further improving the texture in a case where the emulsion composition of the present disclosure is used as an external preparation for skin, the emulsion composition preferably contains at least one kind of liquid oil selected from hydrocarbon oils and at least one kind of liquid oil selected from silicone oils in combination, more preferably contains at least one kind of liquid oil selected from hydrocarbon oils and at least one kind of liquid oil selected from silicone oils, and even more preferably contains at least one kind of liquid oil selected from hydrocarbon oils and at least two kinds of liquid oils selected from silicone oils.

The total content of the liquid oil as Component A with respect to the total amount of the emulsion composition is equal to or greater than 15% by mass.

The emulsion composition of the present disclosure is an oil-in-water type emulsion composition. In a case where the emulsion composition is finely emulsified, the number of emulsion particles containing the liquid oil per unit volume increases, and the distance between the emulsion particles is reduced. It is considered that as a result, the emulsion particles may repel each other and induce particle alignment, viscosity may increase due to the increase in the repulsive force between the particles, and hence a stable gel-type formulation may be formed.

Accordingly, it is preferable that the emulsion composition contains a liquid oil which is capable of aligning the emulsion particles by bringing them to close to each other. In a case where the content of the liquid oil with respect to the total amount of the emulsion composition is equal to or greater than 15% by mass, the emulsion particles become close to each other, and accordingly, the emulsion composition of the present disclosure is in the form of gel having excellent temporal stability. Furthermore, in a case where the content of the liquid oil as Component A is equal to or greater than 15% by mass, moisturizing properties brought about by the liquid oil can be fully obtained.

The total content of the liquid oil as Component A with respect to the total amount of the emulsion composition is preferably equal to or greater than 17% by mass.

From the viewpoint of easily obtaining an emulsion composition having excellent transparency, the content of Component A is preferably equal to or smaller than 40% by mass, and more preferably equal to or smaller than 30% by mass.

Particularly, the emulsion composition preferably contains at least one kind of liquid oil selected from hydrocarbon oils and fatty acid esters and at least one kind of liquid oil selected from silicone oils as Component A, and more preferably contains at least one kind of liquid oil selected from hydrocarbon oils and at least one kind of liquid oil selected from silicone oils as Component A as described above.

Furthermore, an aspect is preferable in which the total amount of at least one kind of liquid oil selected from hydrocarbon oils and fatty acid esters and at least one kind of liquid oil selected from silicone oils is equal to or greater than 15% by mass with respect to the total amount of the emulsion composition. In addition, an aspect is more preferable in which the total amount of at least one kind of liquid oil selected from hydrocarbon oils and at least one kind of liquid oil selected from silicone oils is equal to or greater than 17% by mass with respect to the total amount of the emulsion composition.

More specifically, the emulsion composition contains, as Component A, at least one kind of hydrocarbon oil selected from squalane as a hydrocarbon oil and hydrogenated polyisobutene and at least one kind of silicone oil, more preferably two kinds of silicone oils, selected from dimethicone, methyl trimethicone, caprylyl methicone, and cyclopentasiloxane, in an amount equal to or greater than 15% by mass in total with respect to the total amount of the emulsion composition, and preferably in an amount equal to or greater than 17% by mass in total.

In addition, in a case where a hydrocarbon oil and a silicone oil are used in combination, a content ratio between the hydrocarbon oil and the silicone oil, represented by hydrocarbon oil:silicone oil, is preferably within a range of 1:10 to 10:1 based on mass. From the viewpoint of further improving the texture in a case where the emulsion composition is applied to skin, the content ratio is more preferably 3:1 to 1:3, and even more preferably 2:1 to 1:2.

The content of the silicone oil with respect to the total amount of the liquid oil as Component A contained in the emulsion composition of the present disclosure is preferably 55% by mass to 95% by mass, and more preferably 55% by mass to 90% by mass.

[Component B: nonionic surfactant which is selected from a saturated fatty acid glyceryl and a saturated fatty acid polyglyceryl and has HLB equal to or smaller than 7]

The emulsion composition of the present disclosure contains B: at least one kind of nonionic surfactant which is selected from a saturated fatty acid glyceryl and a saturated fatty acid polyglyceryl (hereinafter, collectively referred to as saturated fatty acid (poly)glyceryl in some cases) and has an HLB equal to or smaller than 7.

Generally, HLB is a parameter showing hydrophilic-lipophilic balance used in the field of surfactant. HLB can be calculated using generally used calculation formulae such as Kawakami's formula represented by Equation (1) and Oda's formula represented by Equation (2).

In a case where the nonionic surfactant to be used is a commercial product, the value of HLB described in the catalog of the commercial product is adopted.

$$HLB = 7 + 11.7 \log(Mw/Mo) \qquad \text{Equation (1)}$$

In Equation (1), Mw represents a molecular weight of hydrophilic groups, and Mo represents a molecular weight of hydrophobic groups.

$$HLB = \frac{\sum \text{Inorganicity value}}{\sum \text{Organicity value}} \times 10 \qquad \text{Equation (2)}$$

In Equation (2), the inorganicity value and the organicity value are characteristic values assigned to the respective compounds described in "Organic Conception Diagram". Regarding the inorganicity value and the organicity value, for example, documents such as "Organic Conception Diagram-Fundamentals and applications-(1984), Yoshio Koda" can be referred to.

Examples of the saturated fatty acid (poly)glyceryl having an HLB equal to or smaller than 7 that is Component B in the present disclosure include esters of monoglycerin or polyglycerin and a saturated fatty acid having 8 to 18 carbon atoms.

Examples of the saturated fatty acid include caprylic acid, capric acid, lauric acid, myristic acid, palmitic acid, and stearic acid.

Examples of the saturated fatty acid (poly)glyceryl having an HLB equal to or smaller than 7 include monoglyceryl monomyristate, diglyceryl monoisostearate, diglyceryl diisostearate, tetraglyceryl monoisostearate, tetraglyceryl distearate, monoglyceryl monostearate, diglyceryl monostearate, diglyceryl distearate, tetraglyceryl monostearate, tetraglyceryl distearate, and the like.

Particularly, from the viewpoint of making the emulsion composition have more appropriate hardness, it is preferable that the emulsion composition contains, as Component B, saturated fatty acid (poly)glyceryl having stearic acid as a saturated fatty acid. As the saturated fatty acid (poly)glyceryl, glyceryl stearate of a grade having an HLB equal to or smaller than 7, such as glyceryl stearate (HLB=3) or glyceryl stearate (HLB=7), is more preferable.

The emulsion composition may contain only one kind of nonionic surfactant having an HLB equal to or smaller than 7 or two or more kinds of nonionic surfactants having an HLB equal to or smaller than 7.

In the emulsion composition of the present disclosure, the content of Component B with respect to the total amount of the emulsion composition is preferably 0.5% by mass to 10% by mass, and more preferably 1.0% by mass to 6.0% by mass.

[Component C: Sucrose Saturated Fatty Acid Ester]

The emulsion composition of the present disclosure contains Component C.

Examples of Component C include esters of sucrose and a saturated fatty acid having 12 to 18 carbon atoms such as lauric acid, myristic acid, palmitic acid, or stearic acid.

More specifically, examples of the sucrose saturated fatty acid ester as Component C include sucrose monolaurate, sucrose dilaurate, sucrose trilaurate, sucrose tetralaurate, sucrose monopalmitate, sucrose dipalmitate, sucrose tripalmitate, sucrose tetrapalmitate, sucrose monomyristate, sucrose dimyristate, sucrose trimyristate, sucrose tetramyristate, sucrose monostearate, sucrose distearate, sucrose tristearate, sucrose tetrastearate, and the like.

Among these, a sucrose saturated fatty acid ester having an HLB equal to or greater than 3 that contains at least one kind of fatty acid selected from stearic acid, myristic acid, palmitic acid, and lauric acid as a fatty acid is preferable, a sucrose saturated fatty acid ester having an HLB equal to or greater than 3 that contains stearic acid as a fatty acid is more preferable, and a sucrose stearic acid ester having an HLB of 5 to 15 is even more preferable.

As the sucrose saturated fatty acid ester, commercial products can be used. As the commercial products, products whose HLB varies with the compositional ratio, such as sucrose fatty acid monoesters and sucrose fatty acid diesters with different degrees of esterification from Mitsubishi-Chemical Foods Corporation and DKS Co., Ltd. are on the market. It is possible to select an ester of a saturated fatty acid among those commercial products according to the purpose and to use the ester as Component C in the emulsion composition.

The emulsion composition may contain only one kind of Component C or two or more kinds of Component C.

In the emulsion composition of the present disclosure, the content of the sucrose saturated fatty acid ester (that is, Component C) with respect to the total amount of the emulsion composition is preferably 0.5% by mass to 10% by mass, more preferably 1.0% by mass to 5.0% by mass, and even more preferably 2.0% by mass to 5.0% by mass.

[Component D: Ionic Surfactant which has Saturated Fatty Acid Residue as Hydrophobic Group and Glutamic Acid Residue as Hydrophilic Group]

The emulsion composition of the present disclosure contains an ionic surfactant (hereinafter, referred to as Component D in some cases) having a saturated fatty acid residue as a hydrophobic group and a glutamic acid residue as a hydrophilic group.

Herein, "residue" refers to a substituent obtained by removing one hydrogen atom from hydrocarbon in a molecule.

Component D is not particularly limited as long as it is an ionic surfactant having a saturated fatty acid residue as a hydrophobic group and a glutamic acid residue as a hydrophilic group.

Examples of the saturated fatty acid include caprylic acid, capric acid, lauric acid, myristic acid, palmitic acid, and stearic acid.

Specifically, examples thereof include acyl glutamate, sodium surfactin, and the like. From the viewpoint of further improving transparency and gel hardness of the emulsion composition, acyl glutamate is preferable.

Examples of the acyl glutamate include sodium cocoyl glutamate, disodium cocoyl glutamate, potassium cocoyl glutamate, triethanolamine cocoyl glutamate, sodium N-lauroyl-L-glutamate, disodium N-lauroyl-L-glutamate, potassium N-lauroyl-L-glutamate, triethanolamine N-lauroyl-L-glutamate, sodium N-myristoyl-L-glutamate, potassium N-myristoyl-L-glutamate, sodium N-stearoyl-L-glutamate, disodium N-stearoyl-L-glutamate, potassium N-stearoyl-L-glutamate, sodium palm fatty acid glutamate, sodium dilauroyl glutamic acid lysine, and the like.

Among these, from the viewpoint of making the emulsion composition have more appropriate hardness, sodium stearoyl glutamate is preferable as Component D. Specifically, examples of the sodium stearoyl glutamate include sodium N-stearoyl-L-glutamate, disodium N-stearoyl-L-glutamate, and the like. As Component D, potassium N-stearoyl-L-glutamate can also be suitably used.

The emulsion composition may contain only one kind of Component D or two or more kinds of Component D.

In the emulsion composition of the present disclosure, the content of Component D with respect to the total amount of the emulsion composition is preferably 0.1% by mass to 2.0% by mass, more preferably 0.2% by mass to 1.0% by mass, and even more preferably 0.4% by mass to 1.0% by mass.

[Component E: At Least One Kind of Surfactant Having Unsaturated Fatty Acid Residue]

The emulsion composition of the present disclosure contains, as Component E, at least one kind of surfactant having an unsaturated fatty acid residue.

The unsaturated fatty acid residue that the surfactant as Component E has is preferably an unsaturated fatty acid residue selected from the group consisting of an α-linolenic acid residue, an eicosapentaenoic acid residue, a docosahexaenoic acid residue, a linoleic acid residue, a γ-linolenic acid residue, an arachidonic acid residue, a docosapentaenoic acid residue, a palmitoleic acid residue, an oleic acid residue, an elaidic acid residue, an erucic acid residue, and the like. Among these, in view of further improving emulsion stability, an unsaturated fatty acid residue selected from the group consisting of an oleic acid residue, linoleic acid residue, an α-linolenic acid residue, and a γ-linolenic acid residue is preferable.

Although the surfactant as Component E is not particularly limited as long as it has an unsaturated fatty acid residue, it is preferable that the surfactant contains at least one kind of surfactant between a nonionic surfactant and an amphoteric surfactant.

Examples of the nonionic surfactant include a polyglycerin unsaturated fatty acid ester, a sorbitan unsaturated fatty acid ester, an unsaturated fatty acid alkanolamide, a polyoxyethylene sorbitan unsaturated fatty acid ester, and the like. From the viewpoint of further increasing the gel hardness of the gel-type oil-in-water emulsion composition to be obtained, a polyglycerin unsaturated fatty acid ester is preferable. Particularly, as the polyglycerin unsaturated fatty acid ester, from the viewpoint of making the emulsion composition have more appropriate hardness, fatty acid (poly)glyceryl having an HLB equal to or smaller than 12 is preferable, and glyceryl oleate (HLB=2.5), polyglyceryl-4 oleate (HLB=6), polyglyceryl-5 oleate (HLB=3), polyglyceryl-6 oleate (HLB=9), polyglyceryl-10 oleate (HLB=12), or the like is more preferable.

From the viewpoint of excellent gel hardness and excellent turbidity, as the polyglycerin unsaturated fatty acid ester, polyglyceryl-4 oleate (HLB=6), polyglyceryl-5 oleate (HLB=3), and polyglyceryl-6 oleate (HLB=9) are preferable.

Examples of the amphoteric surfactant include lecithin, alkyl aminoacetate, alkyl iminodiacetate, alkyl aminopripionate, alkyl iminodipropionacetate, alkyl dimethyl ammonioacetate, alkyl amidopropyl dimethyl ammonioacetate, alkyl sulfobetaine, alkyl amine oxide, and the like. From the viewpoint of texture, lecithin is preferable.

Lecithin has a hydrophilic group and a hydrophobic group in a molecule. Therefore, conventionally, lecithin has been widely used as an emulsifier in the fields of foods, pharmaceutical products, cosmetics, and the like. Industrially, lecithin with a purity equal to or higher than 60% is being used.

In the emulsion composition of the present disclosure, the lecithin described above can also be used. As the lecithin in the emulsion composition, lecithin with a purity equal to or higher than 65% is preferable, and lecithin with a purity equal to or higher than 70% is more preferable. Furthermore, in the emulsion composition, generally, lecithin called high-purity lecithin with a purity equal to or higher than 80% or equal to or higher than 90% is preferably used.

Examples of lecithin include various known lecithins extracted and isolated from biological bodies of plants, animals, and microorganisms. Examples of lecithin include various lecithins derived from plants such as soybean, corn, peanut, rape seeds, and barley, egg yolk, animals such as cows, and microorganisms such as *E. coli*.

Examples of names of compounds as lecithin include glycerolecithin such as phosphatidic acid, phosphatidylglycerin, phosphatidylinositol, phosphatidyl ethanolamine, phosphatidyl methylethanolamine, phosphatidylcholine, phosphaditylserine, bis-phosphatidic acid, and diphosphatidylglycerin (cardiolipin); sphingolecithin such as sphingomyelin; and the like.

Furthermore, examples of lecithin other than the aforementioned high-purity lecithin usable as Component E include enzymatically decomposed lecithin, enzymatically decomposed hydrogenated lecithin, hydroxy lecithin, and the like.

Among these, as the lecithin used in the emulsion composition of the present disclosure, non-hydrogenated lecithin is preferable, lecithin in which the content of phosphatidylcholine is equal to or greater than 30% by mass is more preferable, and lecithin in which the content of phosphatidylcholine equal to or greater than 50% by mass is even more preferable. The upper limit of the content of phosphatidylcholine is not particularly limited. However, from the viewpoint of availability, the upper limit of the content of phosphatidylcholine is equal to or smaller than 99% by mass for example.

Because hydrogenated lecithin does not have an unsaturated fatty acid residue in a molecule, hydrogenated lecithin (International Nomenclature of Cosmetic Ingredients) is not included in the lecithin as Component E of the present disclosure.

The emulsion composition may contain only one kind of Component E or two or more kinds of Component E. Particularly, from the viewpoint of further improving temporal stability, especially, turbidity stability, it is preferable that the emulsion composition contains at least two kinds of Component E.

It is preferable that the emulsion composition contains, as Component E, at least one kind of nonionic surfactant.

It is preferable that the emulsion composition contains, as Component E, at least one kind of amphoteric surfactant.

The emulsion composition of the present disclosure contains at least two kinds of Component E. More specifically, it is more preferable that the emulsion composition of the present disclosure contains at least one kind of nonionic surfactant and at least one kind of amphoteric surfactant.

In the emulsion composition of the present disclosure, from the viewpoint of enabling the obtained emulsion composition to maintain transparency for a longer period of time, a ratio between the content of the nonionic surfactant and the content of the amphoteric surfactant (content of nonionic surfactant:content of amphoteric surfactant) is preferably 0.01:1 to 1:0.01, and more preferably 0.1:1 to 1:0.1 based on mass.

In a case where the emulsion composition contains a polyglycerin fatty acid ester as a nonionic surfactant and lecithin as an amphoteric surfactant, the transparency of the gel-type emulsion composition is further improved and can be maintained for a longer period of time.

In the emulsion composition of the present disclosure, the content of Component E is preferably 0.1% by mass to 5% by mass, more preferably 0.5% by mass to 3% by mass, and even more preferably 0.8% by mass to 2.9% by mass.

[Component F: water]

From the viewpoint of improving transparency, the emulsion composition of the present disclosure contains water.

The water used in the emulsion composition is not particularly limited as long as the water has excellent biocompatibility. As the water, any of purified water, distilled water, deionized water, pure water, and ultrapure water such as Milli-Q water can be used.

Milli-Q water is ultrapure water obtained using a Milli-Q water manufacturing apparatus which is an ultrapure water manufacturing apparatus from Merck.

The content of water in the emulsion composition of the present disclosure can be appropriately adjusted according to the purpose of use of the emulsion composition and the required texture.

(Content Ratio Between Component B and Component E)

The emulsion composition of the present disclosure contains Component A to Component F described above. The content of the Component E to the content of the Component B is preferably 0.1 to 3.0 based on mass.

That is, provided that the content of Component B in the total amount of the emulsion composition is 1, the content of Component E is preferably within a range of 0.1 to 3.0, more preferably within a range of 0.25 to 2.0, even more preferably within a range of 0.5 to 2.0, and still more preferably within a range of 0.5 to 1.5, based on mass.

In a case where the content ratio (mass ratio) of Component E to Component B which contributes to the generation and stabilization of emulsion particles is within the above range, the temporal stability of the obtained emulsion composition is further improved.

[G Component: Other Components]

As long as the effects in the present disclosure can be expressed, the emulsion composition of the present disclosure can contain other components in addition to Component A to Component F described above.

Hereinafter, those other components that the emulsion composition of the present disclosure can contain will be described.

(G-1: at least one kind of water-soluble moisturizer selected from water-soluble alcohol, saccharide, and amino acid)

The emulsion composition can contain at least one kind of water-soluble moisturizer (hereinafter, referred to as component G1 in some cases) selected from a water-soluble alcohol, saccharide, and an amino acid.

In a case where the emulsion composition contains component G1, the transparency and gel hardness of the emulsion composition are further improved, and the temporal stability of the transparency and the temporal stability of the hardness are further improved as well.

As the water-soluble alcohol that the emulsion composition can contain, any of water-soluble alcohols generally used in external preparations for skin and the like can be used. Examples of the water-soluble alcohol that can be incorporated into the emulsion composition include ethanol, glycerin, diglycerin, 1,3-butylene glycol, dibutylene glycol, propylene glycol, and the like.

In the present specification, "water-soluble alcohol" refers to an alcohol which is found not to be separated from water by visual observation after incorporating water of 25° C. into the alcohol in an amount of 1% by mass, stirring the mixture, and allowing the mixture to stand still for 1 hour.

Particularly, a polyhydric alcohol having a Log P value less than 0.2 showing excellent water solubility is preferable. The Log P value is a common logarithm of a 1-octanol/water partition coefficient, and used as a parameter showing the hydrophobicity of an organic compound. The greater the positive Log P value, the higher the hydrophobicity.

The saccharide that the emulsion composition can contain may be monosaccharide or polysaccharide. Generally, any of sugars used in external preparations for skin such as cosmetics can be used.

Examples of the sugars include glucose, sucrose, sorbitol, trehalose, maltose, mannitol, maltotriose, and the like. The sugars may be derivatives. For example, sugar modified with polyoxyethylene (POE) may be used. Examples of POE-modified sugar include POE-10 methyl glucoside, POE-20 methyl glucoside, and the like.

Examples of the amino acid that the emulsion composition can contain include arginine, alanine, glycine, methionine, aspartic acid, lysine, serine, sarcosine, trimethyl glycine, and the like.

Particularly, from the viewpoint of further improving transparency and stability of gel hardness, as component G1, at least one kind of component F selected from ethanol, glycerin, diglycerin, 1,3-butylene glycol, sucrose, sorbitol, trehalose, POE-10 methyl glucoside, and trimethylglycine is preferable.

From the viewpoint of further improving container suitability in a case where the emulsion composition is filled into a container and then jetted, as component G1, at least one kind of selected from glycerin, diglycerin, trehalose, sorbitol, sucrose, POE-10 methyl glucoside, and trimethylglycine is preferable.

The emulsion composition may contain only one kind of component G1 or two or more kinds of component G1.

In a case where the emulsion composition contains component G1, the content of component G1 with respect to the total amount of the emulsion composition is preferably 1% by mass to 50% by mass, and more preferably 2% by mass to 30% by mass.

(G-2: At Least One Kind of Component F Selected from Cholesterol, Cholesterol Derivative, Phytosterol, Phytosterol Derivative, and Higher Alcohol)

The emulsion composition of the present disclosure can contain at least one kind of component F (hereinafter, referred to as component G2 in some cases) selected from cholesterol, a cholesterol derivative, phytosterol, a phytosterol derivative, and a higher alcohol.

In a case where the emulsion composition contains component G2, the transparency and the gel hardness of the emulsion composition are further improved, and the temporal stability of the transparency and the temporal stability of the hardness are further improved as well.

Examples of the cholesterol derivative that the emulsion composition can contain include dihydrocholesterol, dehydrocholesterol, cholesteryl oleate, cholesteryl isostearate, cholesteryl hydroxystearate, POE-5 cholesteryl ether, and the like.

Examples of the phytosterol derivative that the emulsion composition can contain include phytosteryl oleate, phytosteryl isostearate, phytosteryl hydroxystearate, POE-5 phytosteryl ether, and the like.

Examples of the higher alcohol that the emulsion composition can contain include cetanol, myristyl alcohol, cetostearyl alcohol, stearyl alcohol, behenyl alcohol, aralkyl alcohol, isostearyl alcohol, oleyl alcohol, hexyl decanol, octyl dodecanol, decyl tetradecanol, and the like.

Particularly, as component G2, cholestrol, phytosterol, POE-5 phytosteryl ether, isostearyl alcohol, octyl dodecanol, cetanol, and behenyl alcohol are preferable.

The emulsion composition can only one kind of component G2 or two or more kinds of component G2.

In a case where the emulsion composition of the present disclosure contains component G2, the content of component G2 with respect to the total amount of the emulsion composition is preferably 0.1% by mass to 10% by mass, and more preferably 0.5% by mass to 5% by mass.

The emulsion composition of the present disclosure, which contains Component A to Component F described above and preferably further contains component G1, component G2, and the like, contains nanostructured emulsion particles. Therefore, the emulsion composition has excellent transparency, maintains gel hardness for a long period of time, and has excellent temporal stability.

Furthermore, because the emulsion composition is an oil-in-water emulsion composition containing large amounts of liquid oil. Therefore, the emulsion composition has excellent texture in a case where the composition is applied to skin. Accordingly, the emulsion composition of the present disclosure is suitably used in external preparations for skin such as cosmetics.

In the emulsion composition, in addition to Component A to Component F described above as well as component G1 and component G2 preferably used in combination with Component Fs A to F, various components that can be mixed with external preparation for skin such as cosmetics can also be used according to the purpose.

Specifically, examples of those other components include an anti-acne agent, a disinfectant, a whitening agent, a keratin softener, an anti-inflammatory, a blood circulation accelerator, a chelating agent, a pH adjuster, a pH buffer, an ultraviolet absorber, an aromatic, a colorant, an organic solvent, a preservative, and the like. Examples of those other components also include functional components exhibiting useful esthetic effects. Examples of the functional components exhibiting esthetic effects include carotenoid such as astaxanthin, β carotene, zeaxanthin, lycopene, and lutein.

As described above, the emulsion composition of the present disclosure has excellent transparency and high gel hardness. Therefore, the emulsion composition can be suitably used in external preparation for skin such as cosmetics and the like. Particularly, because the emulsion composition is a stable gel-type emulsion composition having high gel hardness, for example, even though the emulsion composition is applied to skin and then reapplied to skin after a passage of time, excellent texture thereof is maintained. Accordingly, in a case where the emulsion composition is repeatedly applied to skin as an external preparation for skin such as cosmetics, the emulsion composition has an advantage of not causing deterioration of texture.

[External Preparation for Skin]

The emulsion composition of the present disclosure is applicable to external preparations for skin. That is, external preparations for skin can contain the emulsion composition of the present disclosure described above.

External preparations for skin can further contain medicinal ingredients required for the external preparations for skin, in addition to the emulsion composition of the present disclosure described above.

Examples of the external preparations for skin, to which the emulsion composition of the present disclosure is suitably applied, particularly include cosmetics such as skin care cosmetics (toner, essence, and the like), cosmetics for body (body lotion and the like), and cosmetics for scalp. The external preparations for skin include pharmaceutical products for treating skin diseases in addition to cosmetics. Here, the use of the emulsion composition of the present disclosure is not limited to the above range.

Containers used for the emulsion composition of the present disclosure or for the external preparations for skin containing the emulsion composition are not particularly limited. From the viewpoint of inhibiting the invasion of germs from the outside air and enabling the emulsion composition or the external preparations for skin to be used for a long period of time in a sterile state, a so-called airless container (normal airless container) or shut off airless container is preferable. In the present disclosure, it is preferable that the emulsion composition is used in a shut off airless container. In a case where the emulsion composition is used in a shut off airless container, it is possible to inhibit precipitation, turbidity change, and the like resulting from drying of the emulsion composition at a jetting portion.

[Manufacturing Method of Emulsion Composition]

The manufacturing method of the emulsion composition of the present disclosure is not particularly limited.

It is preferable that the emulsion composition of the present disclosure having excellent transparency and excellent temporal stability is manufactured by the following manufacturing method.

For example, a suitable manufacturing method of the emulsion composition includes preparing an oil phase composition containing at least one kind of liquid oil selected from a hydrocarbon oil, an aliphatic ester, and a silicone oil (Component A) and at least one kind of nonionic surfactant having an HLB equal to or smaller than 7 that is selected from a saturated fatty acid (poly)glyceryl (Component B) (step (I)), preparing a water phase composition containing a sucrose saturated fatty acid ester (Component C), an ionic surfactant having a saturated fatty acid residue as a hydrophobic group and a glutamic acid residue as a hydrophilic group (Component D), at least one kind of surfactant having an unsaturated fatty acid residue (Component E), and water (Component F) (step (II)), and performing an emulsification treatment on a mixture of the oil phase composition and the water phase composition under the high-pressure condition of a pressure equal to or higher than 100 MPA (step (III)).

In the above example manufacturing method, Component E is used for preparing the water phase composition in the step (II). However, depending on the solubility of Component E, Component E may be used for preparing the oil phase composition in the step (I).

<Step (I): Preparation of Oil Phase Composition>

The step (I) includes obtaining an oil phase composition used for preparing the emulsion composition. In the step (I), for example, Component A, Component B, and an oleaginous component such as component G2 (a cholesterol derivative or a higher alcohol) that is incorporated as desired are mixed together, heated at a temperature of 70° C. to 120° C., and stirred such that Component B and the like are dissolved in Component A, thereby preparing the oil phase composition.

<Step (II): Preparation of Water Phase Composition>

The step (II) includes preparing a water phase composition used in the emulsion composition. In the step (II), for example, Component C, Component D, Component E, Component F, and an aqueous component such as component G1 (a water-soluble moisturizer selected from a water-soluble alcohol, saccharide, an amino acid, and an amino acid derivative) that is incorporated as desired are added to water as Component F, heated at a temperature of 60° C. to 80° C., and stirred such that Component C and the like are dissolved in water (Component F), thereby preparing the water phase composition.

As described above, depending on the physical properties of Component E, Component E may be used in the step (I) by being mixed with an oleaginous component.

<Step (III): Preparation of Emulsion Composition>

The step (III) includes preparing an emulsion composition by mixing together the oil phase composition and the water phase composition obtained as above and emulsifying the mixture. In the step (III), the water phase composition and the oil phase composition obtained through the respective steps described above are mixed together so as to obtain a mixture, and an emulsification treatment is performed on the obtained mixture under the high-pressure condition of a pressure equal to or higher than 100 MPa.

For example, in a case where the emulsification treatment is performed by means of stirring using a stirrer, stirring using an impeller, a homogenizer, or a general emulsification apparatus such as a continuous flow-type shearing machine exploiting shearing action under the general condition, due to insufficient shearing force, sometimes nanostructured emulsion particles are not obtained.

Accordingly, from the viewpoint of transparency of the obtained emulsion composition and temporal stability of gel, it is preferable that the emulsification treatment is performed under the high-pressure condition.

The emulsification treatment under the high-pressure condition is preferably an emulsification treatment of applying high shearing force equal to or higher than 100 MPa. The emulsification treatment is more preferably performed under the condition of a pressure equal to or higher than 150 MPa, and even more preferably performed under the condition of a pressure equal to or higher than 200 MPa.

Examples of stirring means used in the emulsification treatment performed under the high-pressure condition of a pressure equal to or higher than 100 MPa include a high-speed stirring method using a homogenizer, a disper mixer, or an ultramixer, an ultrasonic method using an ultrasound homogenizer, a high-pressure homogenizer method of applying high shearing force by using a high-pressure homogenizer, and the like.

Examples of the ultrasound homogenizer include ultrasound homogenizers US-600, US-1200T, RUS-1200T, and MUS-1200T (manufactured by NISSEI Corporation.), ultrasound processors UIP2000, UIP-4000, UIP-8000, and UIP-16000 (manufactured by Hielscher), and the like. The high-power ultrasound irradiation apparatuses described above are used at a frequency equal to or lower than 25 kHz and preferably at a frequency of 15 kHz to 20 kHz.

Examples of chamber-type high-pressure homogenizers include MICROFLUIDIZER (manufactured by Microfluidics Corporation), NAOMIZER (manufactured by yoshida kikai co., ltd.), ULTIMAIZER (manufactured by SUGINO MACHINE LIMITED), and the like.

Examples of homogenizing valve-type high-pressure homogenizers include a Gaulin-type homogenizer (manufactured by APV), a Lannier-type homogenizer (manufactured by Lannier Company), a high-pressure homogenizer (manufactured by GEA Niro Soavi), a homogenizer (manufactured by SANWA Machinery Trading Co., LTD.), a high-pressure homogenizer (manufactured by IZUMI FOOD MACHINERY), an ultrahigh-pressure homogenizer (manufactured by IKA), and the like.

From the viewpoint of nanostructuring emulsion particles, the operation pressure of the high-pressure homogenizer is preferably equal to or higher than 100 MPa, and more preferably equal to or higher than 200 MPa.

In a case where a mixture is treated once with a high-pressure homogenizer for a high-pressure treatment, the number of passes is regarded as 1. In a case where a mixture is treated twice in total with the same homogenizer or with different homogenizers, the number of passes is regarded as 2.

The number of passes of the high-pressure treatment may be 1. However, from the viewpoint of improving the homogeneity of the obtained emulsion composition, the number of passes is preferably equal to or greater than 2, and more preferably 2 to 8. The temperature of the mixture before the high-pressure dispersion treatment is set to be 20° C. to 80° C., more preferably set to be 40° C. to 70° C.

It is preferable that the emulsion composition is rapidly cooled immediately after the high-pressure dispersion treatment by using cooling means such that the emulsion composition is cooled down to a predetermined temperature. As cooling apparatuses, any of commercial heat exchangers can be used.

In the high-pressure emulsification method, the operation conditions of the emulsification apparatus such as the pressure condition, the temperature condition, and the like described above are not particularly limited because these vary with the specification of the apparatus.

In the manufacturing method as an embodiment of the present disclosure, the emulsification step may include preliminary emulsification. For example, an emulsification treatment is performed by means of stirring using a stirrer or an impeller, a homogenizer, or a general emulsification apparatus such as a continuous flow-type shearing machine exploiting shearing action under the general condition so as to obtain a pre-emulsion, the pre-emulsion is treated with high shearing force under a high-pressure condition such that the pre-emulsion is further emulsified, thereby obtaining a transparent gel-type emulsion composition containing desired nanostructured emulsion particles.

If necessary, the high-shearing force treatment may be repeated.

Furthermore, by manufacturing an emulsion, which contains an oil phase composition at a concentration higher than a concentration in a final emulsion composition of interest, and then diluting the emulsion with water or an aqueous medium, an emulsion composition of a desired concentration can be obtained.

(Other Steps)

In the manufacturing method of the emulsion composition, after the emulsion composition is prepared through the steps described above, if necessary, a sterilization step can be performed.

In a case where the sterilization step is performed, the sterilization step may be performed at the time of preparing the emulsion composition or after the emulsion composition is prepared.

In a case where the sterilization step is performed at the time of preparing the emulsion composition, the sterilization step may be performed at any stage in the respective steps described above. Particularly, it is preferable that the sterilization step is performed at the time of obtaining a mixture by stirring and mixing together the water phase composition and the oil phase composition or performed as soon as possible after the emulsification treatment is performed under the high-pressure condition of a pressure equal to or higher than 100 MPa.

By the aforementioned method, the emulsion composition of the present disclosure having excellent transparency and excellent temporal stability is manufactured.

EXAMPLES

Hereinafter, the present invention will be specifically described based on examples, but the present invention is not limited to the following examples. Hereinafter, unless otherwise specified, "%" is "% by mass".

Example 1 to Example 12

Among the components described in the following Table 1 to Table 3, Component C, Component D, Component E, and Component F were dissolved by being heated for 45 minutes at 70° C., thereby obtaining a water phase composition A.

Component A and Component B described in the following Table 1 to Table 3 were dissolved by being heated for 30 minutes at 70° C., thereby obtaining an oil phase composition A.

While the obtained water phase composition A was being stirred, the obtained oil phase composition A was added to the water phase composition A, and the mixture was treated with ultrasound at a rate of 100 g/l min by using an ultrasound homogenizer (model type: US-600, manufactured by NISSEI Corporation.), thereby obtaining a pre-emulsion.

Then, the obtained pre-emulsion was subjected to high-pressure emulsification at a pressure of 245 MPa by using an ultrahigh-pressure emulsification apparatus (model name: ULTIMAIZER HJP-25001, SUGINO MACHINE LIMITED), thereby obtaining an emulsion composition.

The obtained emulsion composition was evaluated by the following method. The evaluation results are described in the following Table 1 to Table 3. As a comparative example, the formulation and evaluation results of Example 8 are described in Table 3.

Example 13 to Example 16

According to the formulation in Table 4, emulsion compositions were prepared in the same manner as in Example 1. The obtained emulsion compositions were evaluated in the same manner as in Example 1. The evaluation results are described in the following Table 4.

Example 17 to Example 24 and Comparative Example 1 to Comparative Example 4

According to the formulation in the following Table 5 and Table 6, emulsion compositions were prepared in the same manner as in Example 1. The obtained emulsion compositions were evaluated in the same manner as in Example 1. The evaluation results are described in the following Table 5 to Table 7. As a comparative example, the formulation and evaluation results of Example 21 are described in Table 6. Furthermore, as a comparative example, the formulation and evaluation results of Example 24 are described in Table 7.

Example 25 to Example 28

According to the formulation in the following Table 8, emulsion compositions were prepared in the same manner as in Example 1. The obtained emulsion compositions were evaluated in the same manner as in Example 1. The evaluation results are described in the following Table 8. As a comparative example, the formulation and evaluation results of Example 13 are described in Table 8.

Details of the components used for preparing the emulsion compositions described in the following Table 1 to Table 8 are as below.

Squalane (Component A): manufactured by Nikko Chemicals Co., Ltd., purified olive squalane Dimethicone (Component A): manufactured by Shin-Etsu Chemical Co., Ltd., KF-96A 5cs (trade name)

Methyl trimethicone (Component A): manufactured by Shin-Etsu Chemical Co., Ltd., TMF-1.5

Cyclopentasiloxane (Component A): manufactured by Shin-Etsu Chemical Co., Ltd., KF-995

Octyldodecyl myristate (Component A): manufactured by Nikko Chemicals Co., Ltd., NIKKOL (registered trademark, the rest is the same as this) ODM-100

Glyceryl stearate HLB=3 (Component B): Nikko Chemicals Co., Ltd., NIKKOL MGS BV-2

Glyceryl stearate HLB=7 (Component B): Nikko Chemicals Co., Ltd., NIKKOL MGS F20V Sucrose stearic acid ester HLB=5 (Component C): manufactured by Mitsubishi-Chemical Foods Corporation, SURFHOPE SE COSME C-1805

Sucrose stearic acid ester HLB=11 (Component C): manufactured by Mitsubishi-Chemical Foods Corporation, SURFHOPE SE COSME C-1811

Sucrose stearic acid ester HLB=15 (Component C): manufactured by Mitsubishi-Chemical Foods Corporation, SURFHOPE SE COSME C-1815

Sodium stearoyl glutamate (Component D): manufactured by Ajinomoto Healthy Supply Co., Inc., AMISOFT HS-11P Glyceryl oleate (Component E) HLB=2.5: Nikko Chemicals Co., Ltd., NIKKOL (registered trademark) MGO, Polyglyceryl-4 oleate (Component E) HLB=6.0: Nikko Chemicals Co., Ltd., NIKKOL (registered trademark) TETRAGLYN-10V, Polyglyceryl-5 oleate (Component E) HLB=3.0: Taiyo Kagaku Co., Ltd., SUNSOFT A-171E-C, Polyglyceryl-6 oleate (Component E) HLB=9.0: manufactured by Nikko Chemicals Co., Ltd., NIKKKOL (registered trademark) HEXAGLYN-10V, Polyglyceryl-10 oleate (Component E) HLB=12: manufactured by Nikko Chemicals Co., Ltd., NIKKKOL (registered trademark) DECAGLYN-10V, Lecithin (Component E): manufactured by Tsuji Oil Mills co., Ltd., SLP-WHITE, phosphatidylcholine (PC) content: 30% by mass Lecithin (Component E): manufactured by Tsuji Oil Mills co., Ltd., SLP-PC70, PC content: 70% by mass, Lecithin (Component E): manufactured by H. Holstein Co., Ltd., PHOSPHOLIPON (registered trademark) 90G PC content: equal to or greater than 94% by mass, Hydrogenated lecithin (other components): manufactured by Tsuji Oil Mills co., Ltd., SLP-WHITE H

[Performance Evaluation]

The obtained emulsion compositions were evaluated by the following method. The results are described in the following Table 1 to Table 3.

According to the following evaluation standards, rank A to rank C are practically acceptable levels, and rank D is a practically problematic level.

[Appearance]

The obtained emulsion compositions were visually observed to check whether or not the emulsion compositions look like gel.

[Measurement of hardness: initial hardness]

For measuring the hardness of the obtained emulsion compositions, a stress from a sample that occurred in a case where a certain load was applied thereto was detected as a load, and the detected load was adopted as hardness (unit: g).

As a hardness measurement apparatus, a rheometer (FUDOH: RHEOTECH) was used.

The hardness was measured by a method of pressing a disk-like probe (20 φ) on each of the emulsion compositions by 20 mm under a load of 200 g at a speed of 1 mm/sec at 25° C. The maximum load obtained at this time was adopted as hardness, and based on the obtained hardness, the emulsion composition was evaluated based on the following standards.

(Evaluation Standards)

A: The hardness was equal to or higher than 50 g.

B: The hardness was equal to or higher than 25 g and less than 50 g.

C: The hardness was equal to or higher than 10 g and less than 25 g.

D: The hardness was less than 10 g.

[Hardness Stability: Hardness Change]

The obtained emulsion compositions were stored for 1 month at 50° C., and then the hardness of the emulsion compositions was measured by the same method as that used for measuring the initial hardness. Furthermore, a difference between the initial hardness and the hardness after storage was calculated. According to the evaluation, the smaller the difference, the better the temporal stability.

[Hardness Stability: Service Life Lasting Until Hardness Becomes 10 g]

The obtained emulsion compositions were stored at 50° C., and the hardness of the emulsion compositions was regularly measured by the same method as that used for measuring the initial hardness. The hardness was continuously measured until the hardness became 10 g. The hardness is described in Table 1 as a storage period that lasted until the hardness became 10 g (service life lasting until hardness became 10 g).

The hardness stability was evaluated based on the following standards. According to the evaluation, the longer the period of time taken for the hardness to become 10 g, the better the temporal stability. Rank D is a practically problematic level.

(Evaluation Standards)

A: The period of time taken for the hardness to become 10 g was equal to or longer than 3 months.

B: The period of time taken for the hardness to become 10 g was equal to or longer than 2 months and less than 3 months.

C: The period of time taken for the hardness to become 10 g was equal to or longer than 1 month and less than 2 months.

D: The period of time taken for the hardness to become 10 g was less than 1 month.

[Measurement of Turbidity: Initial Turbidity]

By using an ultraviolet-visible spectrophotometer, absorbance and turbidity at a wavelength of 625 nm were measured, and transparency was evaluated based on the following standards.

Turbidity was measured using a commercial ultraviolet-visible spectrophotometer U-2550 (Shimadzu Corporation). That is, each of the emulsion compositions was put into a spectrophotometer cell and measured at an optical path length of 1 cm, and absorbance at a wavelength of 625 nm was adopted as turbidity.

(Evaluation Standards)

A: The turbidity was less than 0.10.

B: The turbidity was equal to or higher than 0.10 and less than 0.25.

C: The turbidity was equal to or higher than 0.25 and less than 0.50.

D: The turbidity was equal to or higher than 0.50.

[Measurement of Turbidity: Turbidity Stability]

The obtained emulsion compositions were stored for 1 month at 50° C., and then the turbidity of the emulsion compositions was measured by the same method as that used for measuring the initial turbidity. Furthermore, a difference between the initial turbidity and the turbidity after storage was calculated and adopted as a turbidity change.

The turbidity stability was evaluated based on the following standards.

(Evaluation Standards)

A: The turbidity change was less than 0.10.

B: The turbidity change was equal to or higher than 0.10 and less than 0.25.

C: The turbidity change was equal to or higher than 0.25 and less than 0.50.

D: The turbidity change was equal to or higher than 0.50.

[Evaluation 1 as External Preparation for Skin]

Ten monitors were asked to use the emulsion compositions of Example 1 to Example 6 as an external preparation for skin by the following method, and asked to evaluate the texture.

First, the monitors were asked to apply 200 μl (microliters) of each of the emulsion compositions to the inside of one forearm, spread the emulsion composition with fingers of the other arm, and evaluate the texture based on the following standards. Among the evaluation ranks selected by the monitors, the evaluation result that the most people chose was adopted as an evaluation rank, and in a case where evaluation results are chosen by the same number of people, a better one was selected.

<Texture: Moistness>

(Evaluation Standards)

A: The emulsion composition was very moist.

B: The emulsion composition was moist.

C: The emulsion composition was not that moist.

D: The emulsion composition was not moist.

<Texture: Stickiness>

(Evaluation standards)

A: The emulsion composition was not sticky.

B: The emulsion composition was not that sticky.

C: The emulsion composition was sticky.

D: The emulsion composition was very sticky.

<Texture: Oiliness>

(Evaluation standards)

A: The emulsion composition was not oily.

B: The emulsion composition was not that oily.

C: The emulsion composition was oily.

D: The emulsion composition was very oily.

<Texture: Comprehensive Evaluation>

(Evaluation Standards)

For each of the evaluation results on moistness, stickiness, and oiliness, 3 points were given to A, 2 points were given to B, and 1 point was given to C. Based on the total score, comprehensive evaluation was performed.

A: The total score for moistness, stickiness, and oiliness was equal to or higher than 8 points.

B: The total score for moistness, stickiness, and oiliness was equal to or higher than 6 points and less than 8 points.

C: The total score for moistness, stickiness, and oiliness was equal to or higher than 4 points and less than 6 points.

D: The total score for moistness, stickiness, and oiliness was less than 4 points.

[Evaluation 2 as External Preparation for Skin]

Ten monitors were asked to use the emulsion compositions of Example 13, Example 17 to Example 24, and Comparative Example 1 to Comparative Example 4 as an external preparation for skin by the following method, and asked to evaluate the texture (skin absorption).

First, the monitors were asked to apply 200 μl (microliters) of each of the emulsion compositions to the inside of one forearm and spread the emulsion compositions with fingers. Then, after 30 minutes, the monitors were asked to reapply 200 μl (microliters) of each of the emulsion compositions to the same site of the inside of one forearm, spread the emulsion composition with fingers, and evaluate the difference between the texture of the initially applied emulsion composition and the texture of the reapplied emulsion composition based on the following standards. Among the evaluation ranks selected by the monitors, the evaluation result that the most people chose was adopted as an evaluation rank, and in a case where evaluation results are chosen by the same number of people, a better one was selected.

<Texture: Skin Absorption>

(Evaluation Standards)

A: In a case where the emulsion composition was reapplied, the emulsion composition was excellently absorbed into skin just as the initially applied emulsion composition, and excellently texture was maintained.

B: In a case where the emulsion composition was reapplied, the emulsion composition was absorbed less into skin compared to the texture of the initially applied emulsion composition.

C: In a case where the emulsion composition was reapplied, the emulsion composition did not easily spread and was poorly absorbed into skin.

TABLE 1

|  |  |  |  | Example 1 | Example 2 | Example 3 | Example 4 | Example 5 |
|---|---|---|---|---|---|---|---|---|
| Formulation of emulsion composition | Component A | Squalane | Hydrogen carbide oil | 20.0% |  | 10.0% | 10.0% | 10.0% |
|  |  | Hydrogenated polyisobutene | Hydrogen carbide oil |  | 20.0% |  |  |  |
|  |  | Dimethicone | Silicone oil |  |  | 10.0% |  |  |
|  |  | Cyclopentasiloxane | Silicone oil |  |  |  |  |  |
|  |  | Methyl trimethicone | Silicone oil |  |  |  | 10.0% |  |
|  |  | Caprylyl methicone | Silicone oil |  |  |  |  | 10.0% |
|  |  | Octyldodecyl myristate | Fatty acid ester |  |  |  |  |  |
|  | Component B | Glyceryl stearate (HLB = 3) |  | 1.5% | 1.5% | 1.5% | 1.5% | 1.5% |
|  | Component C | Sucrose stearic acid ester (HLB = 11) |  | 3.0% | 3.0% | 3.0% | 3.0% | 3.0% |
|  | Component D | Sodium stearoyl glutamate |  | 0.8% | 0.8% | 0.8% | 0.8% | 0.8% |
|  | Component E | Polyglyceryl-5 oleate | Nonionic Lecithin | 1.5% | 1.5% | 1.5% | 1.5% | 1.5% |
|  | Component F | Water |  | Balance | Balance | Balance | Balance | Balance |
|  | Proportion of silicone oil in oil phase % |  |  | 0% | 0% | 50% | 50% | 50% |
| Performance evaluation | Appearance |  |  | Gel | Gel | Gel | Gel | Gel |
|  | Initial hardness | Hardness |  | 47.2 | 42.5 | 50.5 | 50.2 | 51.0 |
|  |  | Evaluation result |  | B | B | A | A | A |
|  | Initial turbidity | Transparency, turbidity |  | 0.22 | 0.21 | 0.14 | 0.13 | 0.15 |
|  |  | Evaluation result |  | B | B | B | B | B |
|  | Texture | Moistness |  | A | A | A | A | A |
|  |  | Stickiness |  | C | C | B | B | B |
|  |  | Oiliness |  | C | C | C | B | C |
|  |  | Comprehensive evaluation |  | C | C | B | B | B |

TABLE 2

|  |  |  |  | Example 6 | Example 7 | Example 8 | Example 9 |
|---|---|---|---|---|---|---|---|
| Formulation of emulsion composition | Component A | Squalane | Hydrogen carbide oil | 7.0% | 2.0% | 7.0% |  |
|  |  | Hydrogenated polyisobutene | Hydrogen carbide oil |  |  |  |  |
|  |  | Dimethicone | Silicone oil | 13.0% | 18.0% | 6.5% | 13.0% |
|  |  | Cyclopentasiloxane | Silicone oil |  |  | 6.5% |  |
|  |  | Methyl trimethicone | Silicone oil |  |  |  |  |
|  |  | Caprylyl methicone | Silicone oil |  |  |  |  |
|  |  | Octyldodecyl myristate | Fatty acid ester |  |  |  | 7.0% |
|  | Component B | Glyceryl stearate (HLB = 3) |  | 1.5% | 1.5% | 1.5% | 1.5% |
|  | Component C | Sucrose stearic acid ester (HLB = 11) |  | 3.0% | 3.0% | 3.0% | 3.0% |
|  | Component D | Sodium stearoyl glutamate |  | 0.8% | 0.8% | 0.8% | 0.8% |
|  | Component E | Polyglyceryl-5 oleate | Nonionic | 1.5% | 1.5% | 1.5% | 1.5% |
|  | Component F | Water |  | Balance | Balance | Balance | Balance |
|  | Proportion of silicone oil in oil phase % |  |  | 65% | 90% | 65% | 65% |
| Performance evaluation | Appearance |  |  | Gel | Gel | Gel | Gel |
|  | Initial hardness | Hardness |  | 51 | 50.2 | 53 | 38.0 |
|  |  | Evaluation result |  | A | A | A | B |
|  | Initial turbidity | Transparency, turbidity |  | 0.10 | 0.08 | 0.09 | 0.12 |
|  |  | Evaluation result |  | A | A | A | B |
|  | Texture | Moistness |  | A | A | A | A |
|  |  | Stickiness |  | B | A | A | B |
|  |  | Oiliness |  | A | B | A | C |
|  |  | Comprehensive evaluation |  | A | A | A | B |

TABLE 3

|  |  |  | Example 10 | Example 11 | Example 8 | Example 12 |
|---|---|---|---|---|---|---|
| Formulation of emulsion composition | Component A | Squalane | 5.3% | 6.0% | 7.0% | 10.5% |
|  |  | Dimethicone | 4.9% | 5.5% | 6.5% | 9.8% |
|  |  | Cyclopentasiloxane | 4.9% | 5.5% | 6.5% | 9.8% |
|  |  | Total | 15.0% | 17.0% | 20.0% | 30.0% |
|  | Component B | Glyceryl stearate (HLB = 3) | 1.5% | 1.5% | 1.5% | 1.5% |
|  | Component C | Sucrose stearic acid ester (HLB = 11) | 3.0% | 3.0% | 3.0% | 3.0% |
|  | Component D | Sodium stearoyl glutamate | 0.8% | 0.8% | 0.8% | 0.8% |

TABLE 3-continued

|  |  |  | Example 10 | Example 11 | Example 8 | Example 12 |
|---|---|---|---|---|---|---|
|  | Component E | Polyglyceryl-5 oleate | 1.5% | 1.5% | 1.5% | 1.5% |
|  | Component F | water | Balance | Balance | Balance | Balance |
|  | Proportion of silicone oil in oil phase % |  | 65% | 65% | 65% | 65% |
| Performance evaluation | Appearance |  | Gel | Gel | Gel | Gel |
|  | Initial hardness | Hardness | 11 | 33 | 53 | 75 |
|  |  | Evaluation result | C | B | A | A |
|  | Initial turbidity | Transparency, turbidity | 0.07 | 0.09 | 0.09 | 0.18 |
|  |  | Evaluation result | A | A | A | B |
|  | Texture | Moistness | A | A | A | A |
|  |  | Stickiness | A | A | A | B |
|  |  | Oiliness | A | A | A | C |
|  |  | Comprehensive evaluation | A | A | A | B |

From the results in Table 1 to Table 3, it is understood that the emulsion compositions of Example 1 to Example 12 are emulsion compositions which have excellent transparency and have gel hardness sufficient for practical use. Particularly, it is understood that in Example 3 to Example 12 containing a hydrocarbon oil and a silicone oil as Component A, the transparency of the emulsion composition is better. Furthermore, it is understood that in Example 6 to Example 12 in which the content of a silicone oil in Component A is within a range of 55% to 95%, the texture (comprehensive evaluation) is much better.

TABLE 4

|  |  |  |  | Example 13 | Example 14 | Example 15 | Example 16 |
|---|---|---|---|---|---|---|---|
| Formulation of emulsion composition | Component A | Squalane | Hydrogen carbide oil | 7.0% | 7.0% | 7.0% | 7.0% |
|  |  | Dimethicone | Silicone oil | 6.5% | 6.5% | 6.5% | 6.5% |
|  |  | Cyclopentasiloxane | Silicone oil | 6.5% | 6.5% | 6.5% | 6.5% |
|  | Component B | Glyceryl sterate | HLB = 3 | 1.5% |  | 1.5% | 1.5% |
|  |  | Glyceryl sterate | HLB = 7 |  | 1.5% |  |  |
|  | Component C | Sucrose stearic acid ester | HLB = 5 |  |  | 3.0% |  |
|  |  | Sucrose stearic acid ester | HLB = 11 | 3.0% | 3.0% |  |  |
|  |  | Sucrose stearic acid ester | HLB = 15 |  |  |  | 3.0% |
|  | Component D | Sodium stearoyl glutamate |  | 0.8% | 0.8% | 0.8% | 0.8% |
|  | Component E | Polyglyceryl-5 oleate | Nonionic | 1.5% | 1.5% | 1.5% | 1.5% |
|  | Component F | Water |  | Balance | Balance | Balance | Balance |
| Performance evaluation | Appearance |  |  | Gel | Gel | Gel | Gel |
|  | Initial hardness | Hardness |  | 53 | 52 | 52 | 51.7 |
|  |  | Evaluation result |  | A | A | A | A |
|  | Initial turbidity | Transparency, turbidity |  | 0.08 | 0.09 | 0.09 | 0.09 |
|  |  | Evaluation result |  | A | A | A | A |
|  | Turbidity stability | Turbidity after 1 M at 50° C. |  | 0.14 | 0.18 | 0.17 | 0.18 |
|  |  | Turbidity change in 1 M at 50° C. |  | 0.06 | 0.09 | 0.08 | 0.09 |
|  |  | Evaluation result |  | A | A | A | A |

From the results in Table 3, it is understood that the emulsion compositions of Example 13 to Example 16 are emulsion compositions which have excellent transparency, gel hardness sufficient for practical use, and excellent turbidity stability.

TABLE 5

|  |  |  |  | Example 17 | Example 18 | Example 19 | Example 20 | Example 21 |
|---|---|---|---|---|---|---|---|---|
| Formulation of emulsion composition | Component A | Squalane | Hydrogen carbide oil | 7.0% | 7.0% | 7.0% | 7.0% | 7.0% |
|  |  | Dimethicone | Silicone oil | 6.5% | 6.5% | 6.5% | 6.5% | 6.5% |
|  |  | Cyclopentasiloxane | Silicone oil | 6.5% | 6.5% | 6.5% | 6.5% | 6.5% |
|  | Component B | Glyceryl stearate (HLB = 3) |  | 1.5% | 1.5% | 1.5% | 1.5% | 1.5% |
|  | Component C | Sucrose stearic acid ester (HLB = 11) |  | 3.0% | 3.0% | 3.0% | 3.0% | 3.0% |
|  | Component D | Sodium stearoyl glutamate | Nonionic | 0.8% | 0.8% | 0.8% | 0.8% | 0.8% |
|  | Component E | Glyceryl oleate | Nonionic | 1.5% |  |  |  |  |
|  |  | Polyglyceryl-4 oleate |  |  | 1.5% |  |  |  |
|  |  | Polyglyceryl-5 oleate |  |  |  | 1.5% |  |  |
|  |  | Polyglyceryl-6 oleate |  |  |  |  | 1.5% |  |
|  |  | Polyglyceryl-10 oleate |  |  |  |  |  | 1.5% |
|  |  | Lecithin (SLP-WHITE/ PC 30%) | Amphoteric |  |  |  |  |  |

TABLE 5-continued

| | | | | Example 17 | Example 18 | Example 19 | Example 20 | Example 21 |
|---|---|---|---|---|---|---|---|---|
| | | Lecithin (SLP-PC70/PC 70%) | | | | | | |
| | | Lecithin (PHOSPHOLIPON 90G/PC 94%) | | | | | | |
| | Other components | Hydrogenated lecithin | | | | | | |
| | F component | water | | Balance | Balance | Balance | Balance | Balance |
| Performance evaluation | Appearance | | | Gel | Gel | Gel | Gel | Gel |
| | Initial hardness | Hardness | | 44 | 51.7 | 53 | 52 | 45 |
| | | Evaluation result | | B | A | A | A | B |
| | Initial turbidity | Transparency, turbidity | | 0.22 | 0.08 | 0.08 | 0.09 | 0.21 |
| | | Evaluation result | | B | A | A | A | B |
| | Turbidity stability | Turbidity after 1 M at 50° C. | | 0.32 | 0.12 | 0.14 | 0.14 | 0.32 |
| | | Turbidity change in 1 M at 50° C. | | 0.10 | 0.04 | 0.06 | 0.05 | 0.11 |
| | | Evaluation result | | B | A | A | A | B |
| | Hardness stability | Hardness after 1 M at 50° C. | | 24 | 35 | 35 | 34 | 26 |
| | | Hardness change in 1 M at 50° C. | | 20 | 17 | 18 | 18 | 19 |
| | | Service life lasting until hardness becomes 10 (unit: month) | | 1.7 | 2.5 | 2.4 | 2.4 | 1.8 |
| | | Evaluation result | | C | B | B | B | C |
| | Texture | Skin absorption | | C | B | B | B | B |

TABLE 6

| | | | | Example 21 | Example 22 | Example 23 | Example 24 |
|---|---|---|---|---|---|---|---|
| Formulation of emulsion composition | Component A | Squalane | Hydrogen carbide oil | 7.0% | 7.0% | 7.0% | 7.0% |
| | | Dimethicone | Silicone oil | 6.5% | 6.5% | 6.5% | 6.5% |
| | | Cyclopentasiloxane | Silicone oil | 6.5% | 6.5% | 6.5% | 6.5% |
| | Component B | Glyceryl stearate (HLB = 3) | | 1.5% | 1.5% | 1.5% | 1.5% |
| | Component C | Sucrose stearic acid ester (HLB = 11) | | 3.0% | 3.0% | 3.0% | 3.0% |
| | Component D | Sodium stearoyl glutamate | Nonionic | 0.8% | 0.8% | 0.8% | 0.8% |
| | Component E | Glyceryl oleate | Nonionic | | | | |
| | | Polyglyceryl-4 oleate | | | | | |
| | | Polyglyceryl-5 oleate | | | 1.5% | 1.5% | 1.5% |
| | | Polyglyceryl-6 oleate | | | | | |
| | | Polyglyceryl-10 oleate | | 1.5% | | | |
| | | Lecithin (SLP-WHITE/PC 30%) | Amphoteric | | | 0.5% | |
| | | Lecithin (SLP-PC70/PC 70%) | | | 0.5% | | |
| | | Lecithin (PHOSPHOLIPON 90G/PC 94%) | | | | | 0.5% |
| | Other components | Hydrogenated lecithin | | | | | |
| | F component | water | | Balance | Balance | Balance | Balance |
| Performance evaluation | Appearance | | | Gel | Gel | Gel | Gel |
| | Initial hardness | Hardness | | 45 | 60.2 | 53.2 | 61 |
| | | Evaluation result | | B | A | A | A |
| | Initial turbidity | Transparency, turbidity | | 0.21 | 0.05 | 0.08 | 0.05 |
| | | Evaluation result | | B | A | A | A |
| | Turbidity stability | Turbidity after 1 M at 50° C. | | 0.32 | 0.09 | 0.16 | 0.08 |
| | | Turbidity change in 1 M at 50° C. | | 0.11 | 0.03 | 0.08 | 0.03 |
| | | Evaluation result | | B | A | A | A |
| | Hardness stability | Hardness after 1 M at 50° C. | | 26 | 46.2 | 35.3 | 45.7 |
| | | Hardness change in 1 M at 50° C. | | 19 | 14 | 18 | 15 |
| | | Service life lasting until hardness becomes 10 (unit: month) | | 1.8 | 3.6 | 2.4 | 3.3 |
| | | Evaluation result | | C | A | B | A |
| | Texture | Skin absorption | | B | A | A | A |

TABLE 7

| | | | | Example 24 | Comp. Ex. 1 | Comp. Ex. 2 | Comp. Ex. 3 | Comp. Ex. 4 |
|---|---|---|---|---|---|---|---|---|
| Formulation of emulsion composition | Component A | Squalane | Hydrogen carbide oil | 7.0% | 7.0% | 7.0% | 7.0% | 7.0% |
| | | Dimethicone | Silicone oil | 6.5% | 6.5% | 6.5% | 6.5% | 6.5% |
| | | Cyclopentasiloxane | Silicone oil | 6.5% | 6.5% | 6.5% | 6.5% | 6.5% |

TABLE 7-continued

|  |  |  | Example 24 | Comp. Ex. 1 | Comp. Ex. 2 | Comp. Ex. 3 | Comp. Ex. 4 |
|---|---|---|---|---|---|---|---|
|  | Component B | Glyceryl stearate (HLB = 3) | 1.5% | 1.5% |  | 1.5% | 1.5% |
|  | Component C | Sucrose stearic acid ester (HLB = 11) | 3.0% | 3.0% | 3.0% |  | 3.0% |
|  | Component D | Sodium stearoyl glutamate | 0.8% | 0.8% | 0.8% | 0.8% |  |
|  | Component E | Glyceryl oleate (Nonionic) |  |  |  |  |  |
|  |  | Polyglyceryl-4 oleate |  |  |  |  |  |
|  |  | Polyglyceryl-5 oleate | 1.5% |  | 1.5% | 1.5% | 1.5% |
|  |  | Polyglyceryl-6 oleate |  |  |  |  |  |
|  |  | Polyglyceryl-10 oleate |  |  |  |  |  |
|  |  | Lecithin (SLP-WHITE/PC 30%) (Amphoteric) |  |  |  |  |  |
|  |  | Lecithin (SLP-PC70/PC 70%) |  |  |  |  |  |
|  |  | Lecithin (PHOSPHOLIPON 90G/PC 94%) | 0.5% |  |  |  |  |
|  | Other components | Hydrogenated lecithin |  |  | 1.5% |  |  |
|  | F component | water | Balance | Balance | Balance | Balance | Balance |
| Performance evaluation | Appearance |  | Gel | Gel | Gel | Liquid | Liquid |
|  | Initial hardness | Hardness | 61 | 24.5 | 22 | 4 | 9 |
|  |  | Evaluation result | A | C | C | D | D |
|  | Initial turbidity | Transparency, turbidity | 0.05 | 0.37 | 0.27 | 0.74 | 0.40 |
|  |  | Evaluation result | A | C | B | D | C |
|  | Turbidity stability | Turbidity after 1 M at 50° C. | 0.08 | — | 0.59 | — | — |
|  |  | Turbidity change in 1 M at 50° C. | 0.03 | — | 0.32 | — | — |
|  |  | Evaluation result | A | — | D | — | — |
|  | Hardness stability | Hardness after 1 M at 50° C. | 45.7 | 11 | — | — | — |
|  |  | Hardness change in 1 M at 50° C. | 15 | 18 | — | — | — |
|  |  | Service life lasting until hardness becomes 10 (unit: month) | 3.3 | 0.5 | — | — | — |
|  |  | Evaluation result | A | D | — | — | — |
|  | Texture | Skin absorption | A | D | — | — | — |

From the results in Table 5 to Table 7, it is understood that the emulsion compositions of Example 17 to Example 24 are emulsion compositions which have excellent transparency just as the emulsion composition of Example 13 and have gel hardness sufficient for practical use.

By the comparison between Example 17 and Example 13, Example 18, and Example 19, it is understood that in a case where polyglyceryl-4 oleate, polyglyceryl-5 oleate, and polyglyceryl-6 oleate are used as Component E, gel hardness, turbidity, and turbidity stability are further improved.

From the evaluation results of Example 19 and Example 22 to Example 24, it is understood that in a case where two kinds of surfactants including a nonionic surfactant and an amphoteric surfactant are used as Component E, all of the gel hardness, turbidity, turbidity stability, and texture are further improved.

In contrast, from the results of Comparative Example 1 to Comparative Example 4, it is understood that in a case where the emulsion composition does not contain any of B component, C component, D component, and Component E, at least any of hardness or turbidity of the emulsion composition is at a practically problematic level.

TABLE 8

|  |  |  | Example 25 | Example 26 | Example 13 | Example 27 | Example 28 |
|---|---|---|---|---|---|---|---|
| Formulation of emulsion composition | Component A | Squalane | 7.0% | 7.0% | 7.0% | 7.0% | 7.0% |
|  |  | Dimethicone | 6.5% | 6.5% | 6.5% | 6.5% | 6.5% |
|  |  | Cyclopentasiloxane | 6.5% | 6.5% | 6.5% | 6.5% | 6.5% |
|  | Component B | Glyceryl stearate (HLB = 3) | 2.5% | 2.0% | 1.5% | 1.0% | 1.0% |
|  | Component C | Sucrose stearic acid ester (HLB = 11) | 3.0% | 3.0% | 3.0% | 3.0% | 3.0% |
|  | Component D | Sodium stearoyl glutamate | 0.8% | 0.8% | 0.8% | 0.8% | 0.8% |
|  | Component E | Polyglyceryl-5 oleate | 0.5% | 1.0% | 1.5% | 2.0% | 3.0% |
|  | Component F | water | Balance | Balance | Balance | Balance | Balance |
|  | B component:E component (content ratio, based on mass) |  | 1:0.2 | 1:0.5 | 1:1 | 1:2 | 1:3 |
| Performance evaluation | Appearance |  | Gel | Gel | Gel | Gel | Gel |
|  | Initial hardness | Hardness | 51.5 | 52.0 | 53 | 50.2 | 50 |
|  |  | Evaluation result | A | A | A | A | A |
|  | Initial turbidity | Transparency, turbidity | 0.09 | 0.09 | 0.09 | 0.09 | 0.13 |
|  |  | Evaluation result | A | A | A | A | B |
|  | Texture | Skin absorption | C | A | A | A | A |

From the results in Table 8, it is understood that the emulsion compositions of Example 25 to Example 28 are emulsion compositions which have excellent transparency just as the emulsion composition of Example 13, have gel hardness sufficient for practical use, and have excellent texture. As is evident from the evaluation results of Example 13 and Example 25 to Example 28, in a case where the content ratio between B component and Component E is within a range of 1:0.25 to 1:2, better results are obtained regarding transparency, gel hardness, and texture.

The disclosure in JP2017-084876 filed on Apr. 21, 2017 is incorporated into the present specification by reference.

All the documents, patent applications, and technical standards described in the present specification are incorporated into the present specification by reference as if each of the documents, the patent applications, and the technical standards is specifically and independently described and incorporated into the present specification by reference.

What is claimed is:

1. A gel-type oil-in-water emulsion composition comprising the following components A to F:
    A: at least one liquid oil which is selected from the group consisting of a hydrocarbon oil, an aliphatic ester and a silicone oil in an amount which is equal to or greater than 15% by mass with respect to a total amount of the gel-type oil-in-water emulsion composition;
    B: at least one nonionic surfactant which is selected from the group consisting of a saturated fatty acid glyceryl and a saturated fatty acid polyglyceryl and which has a Hydrophilic-Lipophilic Balance of equal to or smaller than 7;
    C: a sucrose saturated fatty acid ester;
    D: an ionic surfactant which has a saturated fatty acid residue as a hydrophobic group and a glutamic acid residue as a hydrophilic group;
    E: at least one surfactant having an unsaturated fatty acid residue, wherein component E is one or more kinds of nonionic surfactant; and
    F: water.

2. The gel-type oil-in-water emulsion composition according to claim 1, wherein the unsaturated fatty acid residue of the component E is selected from the group consisting of an oleic acid residue, a linoleic acid residue, and a linolenic acid residue.

3. The gel-type oil-in-water emulsion composition according to claim 1, comprising two or more kinds of the component E.

4. The gel-type oil-in-water emulsion composition according to claim 1, comprising a silicone oil as the component A, wherein a content of the silicone oil is 60% by mass to 95% by mass with respect to a total amount of the component A.

5. The gel-type oil-in-water emulsion composition according to claim 1, comprising, as the components:
    one kind selected from a hydrocarbon oil; and
    two kinds selected from a silicone oil.

6. The gel-type oil-in-water emulsion composition according to claim 1, wherein a content of the component E with respect to a content of the component B in the gel-type oil-in-water emulsion composition is from 0.1 to 3.0% based on mass.

* * * * *